United States Patent

Colman et al.

(10) Patent No.: US 9,612,198 B2
(45) Date of Patent: Apr. 4, 2017

(54) NANO-OPTO-MECHANICAL SENSOR

(71) Applicant: ORIDION MEDICAL 1987 LTD., Jerusalem (IL)

(72) Inventors: Joshua Lewis Colman, Jerusalem (IL); Konstantin Goulitski, Holon (IL); Mark Golberg, Ashdod (IL)

(73) Assignee: Oridion Medical 1987 Ltd., Jerusalem (IL)

( * ) Notice: Subject to any disclaimer, the term of this patent is extended or adjusted under 35 U.S.C. 154(b) by 450 days.

(21) Appl. No.: 14/314,268

(22) Filed: Jun. 25, 2014

(65) Prior Publication Data

US 2015/0377781 A1 Dec. 31, 2015

(51) Int. Cl.
| | |
|---|---|
| *G01N 21/59* | (2006.01) |
| *G01N 21/3504* | (2014.01) |
| *A61B 5/097* | (2006.01) |
| *G01N 33/497* | (2006.01) |
| *G01N 33/00* | (2006.01) |
| *A61B 5/00* | (2006.01) |
| *A61B 5/08* | (2006.01) |
| *A61B 5/083* | (2006.01) |
| *A61B 5/087* | (2006.01) |

(52) U.S. Cl.
CPC .......... *G01N 21/59* (2013.01); *A61B 5/0059* (2013.01); *A61B 5/082* (2013.01); *A61B 5/097* (2013.01); *A61B 5/4836* (2013.01); *G01N 21/3504* (2013.01); *G01N 33/004* (2013.01); *A61B 5/0836* (2013.01); *A61B 5/0873* (2013.01); *A61B 5/6819* (2013.01); *G01N 2201/022* (2013.01); *G01N 2201/061* (2013.01)

(58) Field of Classification Search
CPC ..... A61B 5/0059; A61B 5/082; A61B 5/0836; A61B 5/0873; A61B 5/097; A61B 5/4836; A61B 5/6819; G01N 21/3504; G01N 21/59; G01N 2201/022; G01N 2201/061; G01N 33/004
See application file for complete search history.

(56) References Cited

U.S. PATENT DOCUMENTS

| | | | | |
|---|---|---|---|---|
| 7,127,146 | B2 * | 10/2006 | Schmidt | G01N 21/0303 385/12 |
| 7,248,771 | B2 * | 7/2007 | Schmidt | G01N 21/0303 385/129 |
| 2005/0129573 | A1 * | 6/2005 | Gabriel | B82Y 10/00 422/400 |
| 2008/0021339 | A1 * | 1/2008 | Gabriel | A61B 5/0833 600/532 |

(Continued)

FOREIGN PATENT DOCUMENTS

WO 2008/052104 5/2008

OTHER PUBLICATIONS

Schroeter, J., S. Grumbein, and B. Nestler. "Miniaturization and characterization of a nano flow sensor for intelli-gent implants." Biomed Tech57 (2012): 1.*

(Continued)

*Primary Examiner* — Lisa Caputo
*Assistant Examiner* — Punam Roy

(57) ABSTRACT

There are provided Nano-Opto-Mechanical sensors for measuring concentration of a component in a gas flow, methods for their use and system comprising the same.

20 Claims, 6 Drawing Sheets

(56) References Cited

U.S. PATENT DOCUMENTS

| | | | |
|---|---|---|---|
| 2008/0071154 A1* | 3/2008 | Hausmann | A61B 5/0059 600/323 |
| 2008/0077035 A1* | 3/2008 | Baker | A61B 5/0836 600/532 |
| 2009/0156932 A1* | 6/2009 | Zharov | A61B 5/0059 600/437 |
| 2012/0183949 A1 | 7/2012 | Hyde | |
| 2012/0238848 A1* | 9/2012 | Hausmann | A61B 5/0059 600/328 |
| 2016/0151009 A1* | 6/2016 | Rudmann | G01N 21/3504 600/322 |

OTHER PUBLICATIONS

Barrios, Carlos Angulo. "Optical slot-waveguide based biochemical sensors." Sensors 9.6 (2009): 4751-4765.*

Shahmoon et al., (2010) All-optical nano modulator, sensor, wavelength converter, logic gate, and flip flop based on a manipulated gold nanoparticle J Nanophoton 4(1): 041780.

Mao et al., (2013) Design of nano-opto-mechanical reconfigurable photonic integrated circuit. Journal of Lightwave Technology 31(10): 1660-1669.

* cited by examiner

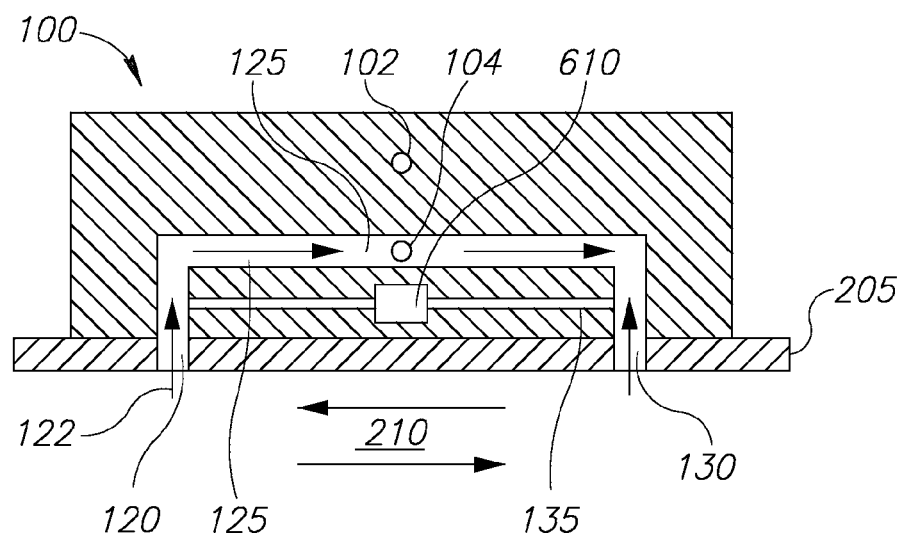
FIG. 6
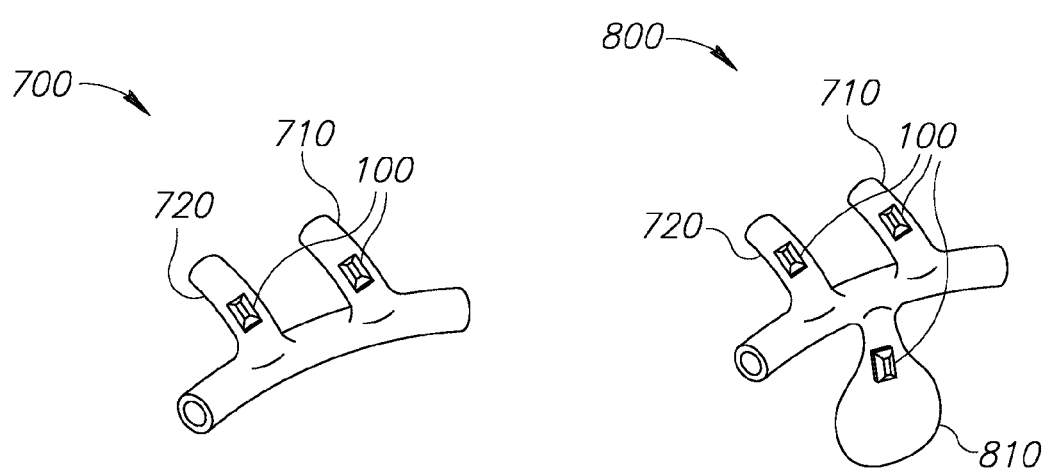
FIG. 7
FIG. 8

NANO-OPTO-MECHANICAL SENSOR

TECHNICAL FIELD

The present disclosure relates to the field of Nano-Opto-Mechanical (NOM) sensors, and more particularly to a NOM sensor configured to measure concentration of a component in a gas flow.

BACKGROUND

Capnography is the monitoring of the concentration or partial pressure of carbon dioxide ($CO_2$) in the respiratory gases. It is usually presented as a graph of expiratory $CO_2$ plotted against time. A capnogram is a direct monitor of the inhaled and exhaled concentration or partial pressure of $CO_2$, where $CO_2$ absorbs infra-red radiation and the presence of $CO_2$ in the gas leads to a reduction in the amount of light falling on a sensor.

In a mainstream capnograph, a sample cell is inserted in the airway between the breathing circuit and an endotracheal tube. A lightweight infrared sensor is attached to the airway adapter. The sensor emits infrared light through the adapter windows to a photodetector typically located on the other side of the airway adapter. The light intensity absorbed by the photodetector is a measure of the end tidal $CO_2$.

In a side-stream capnograph, a $CO_2$ sensor is located in an external main unit and a pump aspirates gas samples from the patient's airway through a long capillary tube into the external main unit. The required sampling flow rate may be high (>400 ml.min-1) where optimal gas flow is considered to be 50-200 ml.min-1 to ensure that the capnographs are reliable in both children and adults.

SUMMARY

The following embodiments and aspects thereof are described and illustrated in conjunction with systems, tools and methods which are meant to be exemplary and illustrative, not limiting in scope.

The current disclosure, in embodiments thereof, is directed to Nano-Opto-Mechanical (NOM) sensors for measuring components in a gas such as but not limited to a concentration of $CO_2$ in exhaled breath. The NOM sensors disclosed herein may advantageously reduce the size and weight of exhaled $CO_2$ monitoring devices. This may reduce the amount of consumed energy to a few nano Watts (according to some embodiments less than 100 nano Watts), and enable the use of small volumes of breath for sampling. Furthermore, due to the high sensitivity of the disclosed NOM sensor, the required gas flow rate may be significantly reduced and may therefore obviate the need for using pumps to withdraw the samples.

In addition, the nano-sized NOM sensor may advantageously facilitate positioning the sensor in the main flow of exhaled air and even as an implant in the patient's airway, including airways of infants; and may be used to measure exhaled $CO_2$ in both intubated and non-intubated patients.

There is provided according to some embodiments, a Nano-Opto-Mechanical (NOM) sensor for measuring concentration of a component in a gas flow, the sensor including: a bypass channel fluidly connected to a gas sampling member, the gas sampling member configured to sample gas flow; a nano-scale void; at least one nano-particle confined in said nano-scale void; a first optical element and a first multimode interference (MMI) region configured to guide a first light beam through the nano-scale void from a first side thereof; and a second optical element and a second MMI region configured to guide a second light beam through the bypass channel and through the nano-scale void from an opposing side thereof.

According to some embodiments, the first and second light beams may be configured to generate interference fringes affecting the location of the nano-particle within the nano-scale void. According to some embodiments, the location of the nano-particle may be indicative of the concentration of the measured component in the sampled gas.

According to some embodiments, the NOM sensor may further include a detection member configured to detect the location of the nano-particle. According to some embodiments, the detection member may be configured to detect a change in the location of the nano-particle within the nano-scale void. According to some embodiments, the detection member may include a third optical element configured to guide a third light beam through the nano-scale void. According to some embodiments, the output intensity of the third light beam may be indicative of the concentration of the gas component. According to some embodiments, detecting the location of the nano-particle may include detecting the output intensity of the third light beam. According to some embodiments, the third light beam may be configured to pass through said nano-scale void in a substantially perpendicular direction relative to the direction of the first and second light beams.

According to some embodiments, the nano-particle comprises gold.

According to some embodiments, the gas may be exhaled breath and the gas component may be exhaled $CO_2$. According to some embodiments, the location of the nanoparticle is indicative of the exhaled $CO_2$ concentration.

According to some embodiments, the first and second light beams may be generated by a single light source split into two light beams. According to some embodiments, the first and second light beams may be light beam an infra-red (IR) light beam.

According to some embodiments, the first, second and third light beams may generated by one or more light sources embedded in the NOM sensor.

According to some embodiments, the NOM sensor may include a flow sensor configured to measure the total gas flow. According to some embodiments, the third light output intensity and the flow sensor measurements may be used to generate a temporal $CO_2$ volumetric flow rate parameter of breathing.

According to some embodiments, at least two nano-particles may be confined in the nano-scale void.

According to some embodiments, there is provided a breath sampling system including: an oral/nasal cannula configured to sample breath flow from a subject; and one or more Nano-Opto-Mechanical (NOM) sensors for measuring concentration of a component in a gas flow.

According to some embodiments, the sensor may include: a bypass channel fluidly connected to said oral/nasal cannula; a nano-scale void; at least one nano-particle confined in the nano-scale void; a first optical element and a first multimode interference (MMI) region configured to guide a first light beam through said nano-scale void from a first side thereof; and a second optical element and a second MMI region configured to guide a second light beam through the bypass channel and through the nano-scale void from an opposing side thereof, According to some embodiments, the first and second light beams may be configured to generate interference fringes affecting the location of the nano-particle in the nano-scale void. According to some embodiments, the location of the nano-particle may be indicative of the concentration of the measured component in the sampled gas.

According to some embodiments, the oral/nasal cannula may include an oral mouthpiece, and one or two nasal prongs. According to some embodiments, the system may include a NOM sensor for each one of the oral mouthpiece and one or two nasal prongs, for measuring oral and nasal exhaled $CO_2$ concentration, respectively.

According to some embodiments, the system may include a detection member configured to detect the location of the nano-particle in the nano-scale void. According to some embodiments, the detection member may include a third optical element configured to guide a third light beam through the nano-scale void. According to some embodiments, the output intensity of said third light beam may be a function of exhaled $CO_2$.

According to some embodiments, the detection member may be configured to detect a change in the location of said nano-particle.

According to some embodiments, detecting the location of the nano-particle may include detecting the output intensity of the third light beam.

According to some embodiments, there is provided a method for measuring concentration of a component in a gas flow, the method including: flowing a gas sample through a bypass channel to a nano-scale void of a Nano-Opto-Mechanical (NOM) sensor, the nano-scale void having a nano-particle therewithin; guiding a first light beam through the nano-scale void from a first side thereof; guiding a second light beam through the nano-scale void from an opposing side thereof; and determining the concentration of the measured component in the sampled gas based on the location of said nano-particle in said nano-scale void.

According to some embodiments, the component in the gas flow is exhaled $CO_2$.

According to some embodiments, determining the concentration of the measured component in the sampled gas may be based on a change in the location of the nano-particle within the nano-scale void.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

In addition to the exemplary aspects and embodiments described above, further aspects and embodiments will become apparent by reference to the figures and by study of the following detailed description.

BRIEF DESCRIPTION OF THE FIGURES

In the following description, various aspects of the disclosure will be described. For the purpose of explanation, specific configurations and details are set forth in order to provide a thorough understanding of the disclosure. However, it will also be apparent to one skilled in the art that the embodiments may be practiced without specific details being presented herein. Furthermore, well-known features may be omitted or simplified in order not to obscure the disclosure. The figures are listed below.

FIG. 6 schematically illustrates the exploded cross section of the NOM sensor with a pneumatic flow meter (differential pressure sensor), according to some embodiments;

FIG. 7 schematically illustrates the nasal cannula system, according to some embodiments;

FIG. 8 schematically illustrates the nasal-oral cannula system, according to some embodiments;

DETAILED DESCRIPTION

Figure 1:
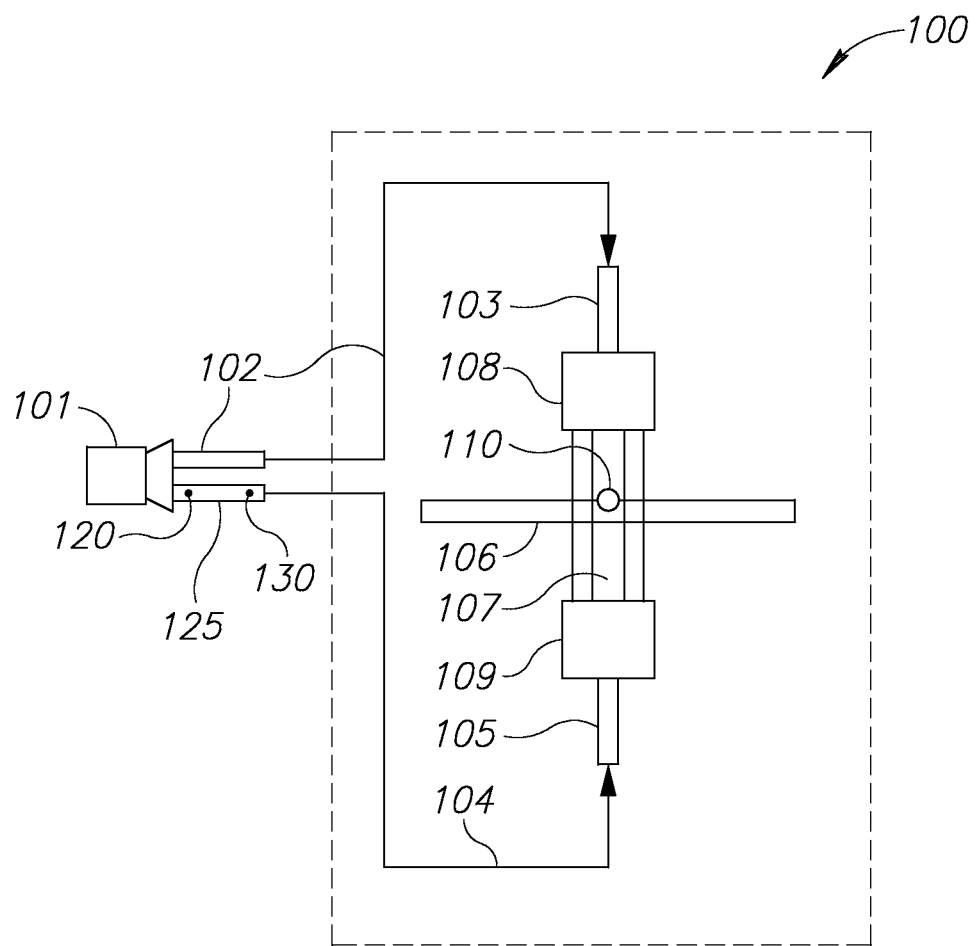
FIG. 1 schematically illustrates a Nano-Opto-Mechanical (NOM) sensor for measuring concentration of a component in a gas flow, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

There is provided herein, according to some embodiments, a Nano-Opto-Mechanical (NOM) sensor for measuring concentration of a component in a gas flow, a nasal cannula system and a mechanical ventilation method. The NOM sensor may include a bypass channel fluidly connected to a gas flow in a gas sampling member, a nano-scale void (which may be referred to as an air gap) positioned in or otherwise associated with the gas sampling member, and at least one nano-particle confined in the nano-scale void.

As used herein, the term "gas sampling member" may refer to a patient interface configured to receive breath samples from the patient. Non-limiting examples of gas sampling members include, nasal cannulas, oral cannulas, oral/nasal cannulas, airway adaptors or any other element configured to receive gas samples from a patient.

The NOM sensor may include a first optical element and a first multimode interference (MMI) region configured to guide a first light beam through one side of the nano-scale void and a second optical element and a second MMI region configured to guide a second light beam through the bypass channel and through the opposing side of the nano-scale void.

As used herein, the term "optical element" may refer to waveguide configured to guide and/or direct a light beam, such as but not limited to an optic fiber.

The first and second light beams may be configured to generate interference fringes in the MMI regions and the nano-scale void. The nano-particle location in the nano-scale void may be affected by the generated interference fringes, and the location of the nano-particle may be indicative of the concentration of the measured component in the gas flow.

The NOM sensor may include a detection member As used herein, the term "detection member" may refer to any element configured to detect the location of the nano-particle in the nano scale void, Optionally, the detection member may include a third optical element configured to guide a third light beam through the nano-scale void, wherein the output intensity of the third light beam may be a function of the gas component. The third light beam may be configured to pass through the nano-scale void in substantially perpendicular direction to the first and second light beams. According to some embodiments, the output detector may include a light detector, (such as but not limited to a charge-coupled device) configured to detect the output intensity of the third light beam.

According to some embodiments, the disclosed NOM gas sensor may not require a pump to aspirate gas samples from the patient's airway as with side stream capnographs that use pumps to aspirate gas through a long capillary tube into an external unit.

In some embodiments, the disclosed NOM sensor may be used in both intubated and non-intubated patients.

According to some embodiments, the term "MMI region" refers to a multimode interference region generated in widened optical waveguides such as silicon waveguides used in passive and/or active waveguide-based devices, such as optical couplers, switches, and the like. However, other optical waveguides are also under the scope of the disclosure.

Reference is now made to FIG. 1, which schematically illustrates a NOM sensor for measuring concentration of a component in a gas flow, according to some embodiments. NOM sensor 100 includes two MMI regions 108 and 109, a nano-scale void 107 located between the two MMI regions 108 and 109 and at least one nano-particle 110 confined in the nano-scale void. The two MMI regions 108 and 109 shown in FIG. 1, may receive light beams through optical elements 102 and 104 and through single mode waveguides 103 and 105, where the two MMI regions 108 and 109 are configured to generate controllable standing waves in nano scale void 107. The diameter of Nano particle 110 may be about few tens of nanometers, typically, in the range of 30 to 100 nanometers (for example, 30-50 nanometers, 40-70 nanometers, 30-80 nanometers or 60-100 nanometers). The size of nano scale void 107 may typically be in the range of 10-100 by 200-1000 nanometers (for example, 10 by 100 nanometers, 50 by 200 nanometers, 80 by 265 nanometers). According to some embodiments, the gas component may be exhaled $CO_2$. However, other components of a gas and atoms may be detected with other embodiments of the disclosed NOM sensor, as further detailed below.

NOM sensor 100 includes a bypass channel 125 and an inlet/outlet hole 120 and an outlet/inlet hole 130. Optionally, NOM sensor 100 may include a light source 101 configured to generate two light beams configured to pass through optical elements 102 and 104. Optionally, NOM sensor 100 may be configured to generate a third light beam configured to pass through optical element 106. Alternatively, one or more light beams may be generated by external light sources and guided to NOM sensor 100 by optical fibers (not shown). NOM sensor 100 includes a first optical element 102, configured to guide a first light beam through nano-scale void 107, a second optical element 104, configured to guide light beam through bypass channel 125, and to next guide the light beam through nano-scale void 107. NOM sensor 100 may include a third optical element 106, configured to guide a third light beam through nano-scale void 107, wherein the output of third light beam is a function of the concentration of a component in a gas flow, (such as, exhaled $CO_2$), that flows in and out of bypass channel 125. The optical elements, 102, 104, and 106 may be single mode silicon waveguides, typically having about 450 nanometer width and about 250 nanometer height, for example, however other optical elements' widths and heights may be designed or manufactured and are included within the scope of this disclosure. However, other waveguides and/or optical fibers may also be applicable and such fall within the scope of the disclosure.

Optionally, nano particle 110 may be a gold nano-particle, however, other nano-particle materials may be used in embodiments of the disclosure and are in the scope of the present disclosure.

The position of Nano-particle 110 in nano scale void 107 is configured to modify intensity of the third light beam output. Nano scale shifts of nano-particle 110 (only on the order of tens of nanometers) may change the light beam output intensity by orders of magnitudes.

The first and the second light beams are configured to generate interference fringes in the two MMI regions and nano-scale void 107. Nano-particle 110 position in nano scale void 107 is affected by the generated interference fringes, in that the nano-particle is trapped by and follows a high intensity fringe.

The third light beam may be configured to pass through nano-scale void 107 in substantially perpendicular direction to the first and second light beams directions. Other crossing angles between the third light beam and the first and second light beams may be envisaged and are in the scope of the present disclosure.

Since the required movement of nano particle 110 in nano-scale void 107 is miniscule (on the nanometer scale) and the size of the nano particle is miniscule, the disclosed NOM sensor sensitivity is high and even small changes in the second light beam intensity, or phase, may drastically affect the third light beam output intensity. Due to the high sensitivity of the NOM sensor, the size of the light sources may be reduced, the energy of the light beam may be reduced to a few nano Watts and the $CO_2$ gas sample volume to be measured by the NOM sensor may be reduced, by a factor of 100, to about 0.2-1 ml/min (e.g. 0.5 ml/min) which is an important advantage of the instant disclosure.

NOM sensor 100, including nano scale void 107, optical elements 102 and 104 and MMI regions 108 and 109, may be fabricated on silicon wafers with submicron resolution using silicon on insulator (SOI) technology. Gold nano particles may be inserted to the fabricated nano-scale void 107, using atomic force microscope (AFM) tip.

Figure 2A:
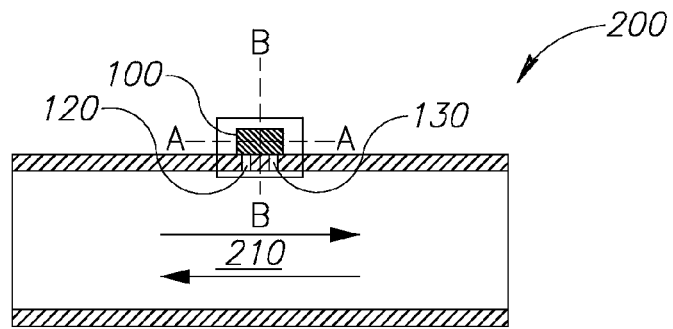
FIG. 2A schematically illustrates a sampling member and a NOM sensor, according to some embodiments.

Reference is now made to FIG. 2A, which schematically illustrates part of a sampling member 200 (such as part of a nasal cannula as shown in FIG. 7 hereinbelow) and a NOM sensor 100, according to some embodiments. NOM sensor 100 is configured to receive breath samples from the main breathing flow 210 flowing in sampling member 200. Thus, part of patient's breathing flow enters from sampling member 200 to a bypass channel (not shown) of NOM sensor 100 through inlets 120 and 130 in wall 205 of sampling member 200, as further described herein, for sampling by NOM sensor 100. It is understood to one of ordinary skill in the art that during exhalation, the breath flow is flowing in one direction (e.g. from inlet 120 to inlet 130 as illustrated by arrows 122—inlet 130 is thus in fact serving as an outlet) and during exhalation in the opposite direction.

Figure 2B:
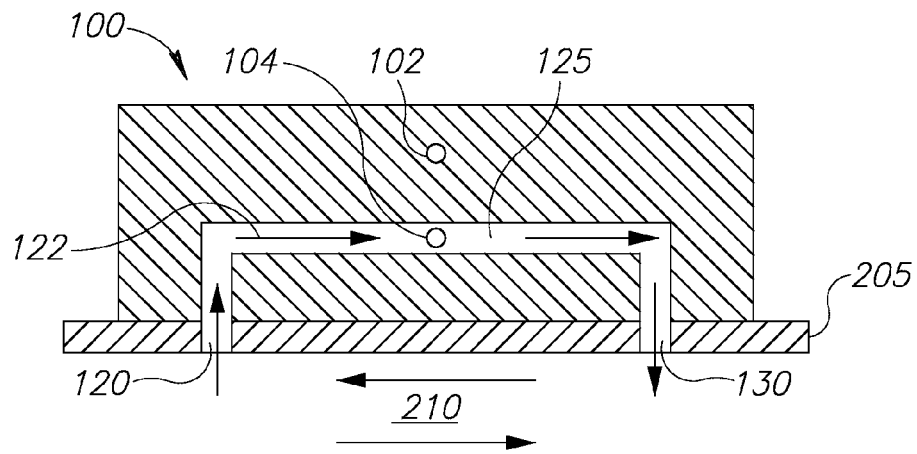
FIG. 2B schematically illustrates an exploded cross section of the NOM sensor, according to some embodiments.

Reference is now made to FIG. 2B, which illustrates a cross section of NOM sensor 100 along line A-A, shown in FIG. 2A, according to some embodiments. Due to a pressure drop between inlets 120 and 130 (configured to receive inhaled and exhaled air, respectively—breathing flow 210, switches direction during inhaling and exhaling), exhaled breath flows into bypass channel 125 of NOM sensor 100. Optical elements 102 and 104 are configured to guide light beams through MMI regions 108 and 109 (illustrated in FIG. 1) and through a nano-scale void (illustrated as 107 in FIG. 2C) from opposite sides thereof, thereby generating interference fringes. Optical fiber 104 is further configured to guide the light beam through bypass channel 125 prior to reaching the nano-scale void. Accordingly, $CO_2$, present in the patient's breath flowing in bypass channel 125, may absorb light that reduces the intensity of the light beam passing there through and hence modifies the generated interference fringes.

Figure 2C:
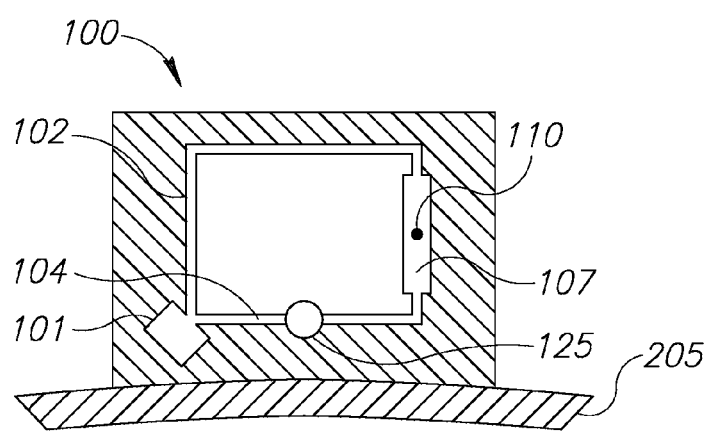
FIG. 2C schematically illustrates an exploded top view of the NOM sensor, according to some embodiments.

Reference is now made to FIG. 2C, which schematically illustrates a cross section of NOM sensor 100 along line B-B, shown in FIG. 2A, according to some embodiments. NOM sensor 100 may include a light source 101. Alternatively, light source 101 may be an external light source in which case optical fiber lines may transmit the light beams to NOM sensor 100 (option not shown). The output beam of light source 101 may be split into two light beams configured to be guided by optical elements 102 and 104. Optical elements 102 and 104 are configured to guide light beams through MMI regions 108 and 109 (illustrated in FIG. 1) and through nano-scale void 107 from opposite sides thereof, thereby generating interference fringes. Optical fiber 104 is further configured to guide the light beam through bypass channel 125 prior to reaching nano-scale void 107. In effect, when the concentration of $CO_2$ is negligible, the generated interference fringes remains unchanged and nanoparticle 110 is positioned in the center of nano-scale void 107, as shown in FIG. 2C. In the nano-scale void center position, nanoparticle 110 scatters most of a third light beam passed through optical element (illustrated as element 106 in FIG. 1), thereby reducing the output intensity of the third light beam, to a substantially zero level.

The temporal variations of exhaled $CO_2$ concentration in bypass channel 125 is typically between 4% (end tidal exhaled $CO_2$ concentration), to 0.04% (inhaled $CO_2$ concentration). $CO_2$ molecules absorb IR light beam, thereby reducing the output intensity proportionally to the $CO_2$ concentration in bypass channel 125. This in turn modifies the interference fringes in nano-scale void 107, and as a result thereof, the position of nano-particle 110 in nano-scale void 107. Consequently, the third light beam output intensity is reduced. Hence, the third light beam output intensity may serve as an indicator of concentration of $CO_2$ in bypass channel 125. Due to the miniscule nano-opto-mechanical effect, the sensitivity of the disclosed $CO_2$ sensor is high and exhaled $CO_2$ flow samples of only about 0.2-1 ml/min (e.g. 0.5 ml/min) may suffice to generate a reliable measurement of exhaled $CO_2$ concentration.

Figure 3:
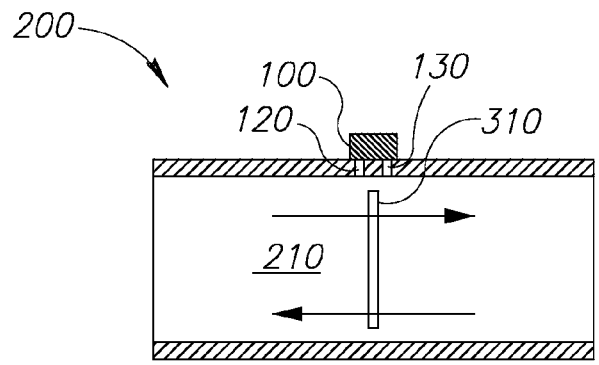
FIG. 3 schematically illustrates the cannula and the NOM sensor with a restrictor, according to some embodiments.

Reference is now made to FIG. 3, which schematically illustrates part of a sampling member 200 (such as part of a nasal cannula as shown in FIG. 7 hereinbelow) and a NOM sensor 100, according to some embodiments. NOM sensor 100 is configured to receive breath samples from the main breathing flow 210 flowing in sampling member 200. Thus, part of patient's breathing flow enters from sampling member 200 to a bypass channel (not shown) of NOM sensor 100 through inlets 120 and 130 in wall 205 of sampling member 200, as further described herein, for sampling by NOM sensor 100.

Restrictor 310 is placed between inlet 120 and 130 of bypass channel 125 (as shown in FIG. 2B) thereby increasing the pressure drop in the main breathing flow of sampling member 200 and thus increasing air flow through bypass channel 125 (shown in FIG. 2B).

Figure 4:
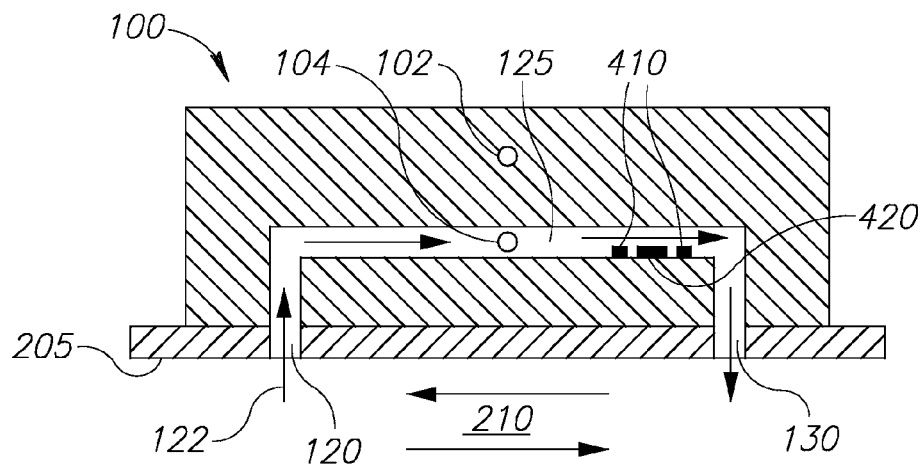
FIG. 4 schematically illustrates the exploded cross section of the NOM sensor with a thermal flow meter in the bypass channel, according to some embodiments.

Reference is now made to FIG. 4, which illustrates a cross section of NOM sensor 100 along line A-A, shown in FIG. 2A, according to some embodiments. Due to pressure drop between inlets 120 and 130 exhaled breath (illustrated by arrow 122) flows into bypass channel 125 of NOM sensor 100, as essentially described herein. Optical elements 102 and 104 are configured to guide light beams through MMI regions 108 and 109 (illustrated in FIG. 1) and through a nano-scale void 107 from opposite sides thereof (illustrated in FIG. 2C), thereby generating interference fringes. Optical fiber 104 is further configured to guide the light beam through bypass channel 125 prior to reaching the nano-scale void. Accordingly, $CO_2$ present in the patient's breath flowing in bypass channel 125 may absorb light that reduces the intensity of the light beam passing there through and hence modifies the generated interference fringes.

Optionally, a thermal flow meter 410 and a heater 420 may be mounted in bypass channel 125 and are configured to measure the gas flow through bypass channel 125. The gas flow through bypass channel 125 is correlated with the flow 210 in sampling member 200, and as such is representative thereof.

Figure 5:
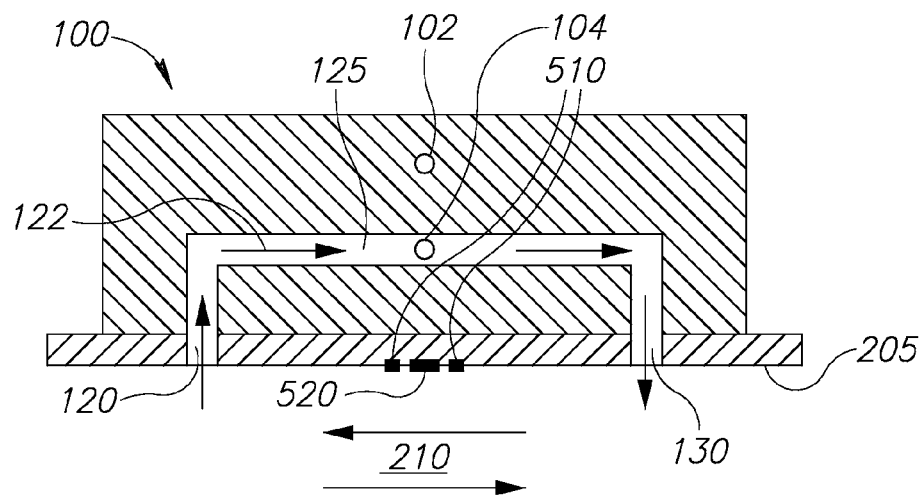
FIG. 5 schematically illustrates the exploded cross section of the NOM sensor with thermal flow meter in the main cannula flow, according to some embodiments.

Reference is now made to FIG. 5, which schematically illustrates an exploded cross section of the NOM sensor 100, as in FIG. 4, with a thermal flow meter 510 and a heater 520 attached to a wall 205 of sampling member 200, according to some embodiments. Thermal flow meter 510 and heater 520 are thus configured to directly monitor the main breathing flow 210.

It is understood that the simultaneous measurements of the total gas flow in bypass channel 125 (FIG. 4), or main breathing flow 210 (FIG. 5), and the exhaled $CO_2$ may be used to define and calculate a $CO_2$ volumetric flow rate parameter of breathing. The $CO_2$ volumetric flow rate parameter as a function of time may be used to generate a capnogram.

Reference is now made to FIG. 6, which schematically illustrates a cross section of a NOM sensor (essentially similar to NOM sensor 100 of FIG. 2B) with a pneumatic flow meter 610 (differential pressure sensor), according to some embodiments. Pneumatic flow meter 610 is configured to measure the pressure drop between the inlets 120 and 130. NOM sensor 100 includes two bypass channels 125 and 135 fluidly connected to inlets 120 and 130. Bypass channel 135 is further connected to pneumatic flow meter 610. The, optionally simultaneous, measurements of the total gas flow in bypass channel 135 (indicative of total flow in sampling member 200), received from pneumatic flow meter 610, and the exhaled $CO_2$ measurement of NOM sensor 100, may be used to define and calculate a $CO_2$ volumetric flow rate parameter of breathing.

Reference is now made to FIG. 7, which schematically illustrates a nasal cannula system 700, according to some embodiments. Nasal cannula system 700 may include a central body comprising prongs 710 and 720, configured to be placed in a patients' nostrils (not shown). Two NOM sensor 100 may be mounted on the walls of prongs 710 and 720, respectively. NOM sensors 100 may thus measure exhaled $CO_2$ concentration of a spontaneously breathing non-intubated patient taking advantage of the small size, small gas volume samples and energy consumption of the disclosed NOM sensor.

Reference is now made to FIG. 8, which schematically illustrates an oral-nasal cannula system 800, according to some embodiments. Cannula system 800 includes a central body comprising prongs 710 and 720, configured to be placed in a patients' nostrils (not shown) and an oral mouthpiece 810, wherein a third NOM sensor 100 is mounted on oral mouthpiece 810, and is configured to measure oral exhaled $CO_2$ concentration.

Cannula systems 700 and 800 may be utilized for monitoring exhaled $CO_2$ concentration of spontaneously breathing non-intubated patients.

Figure 9:
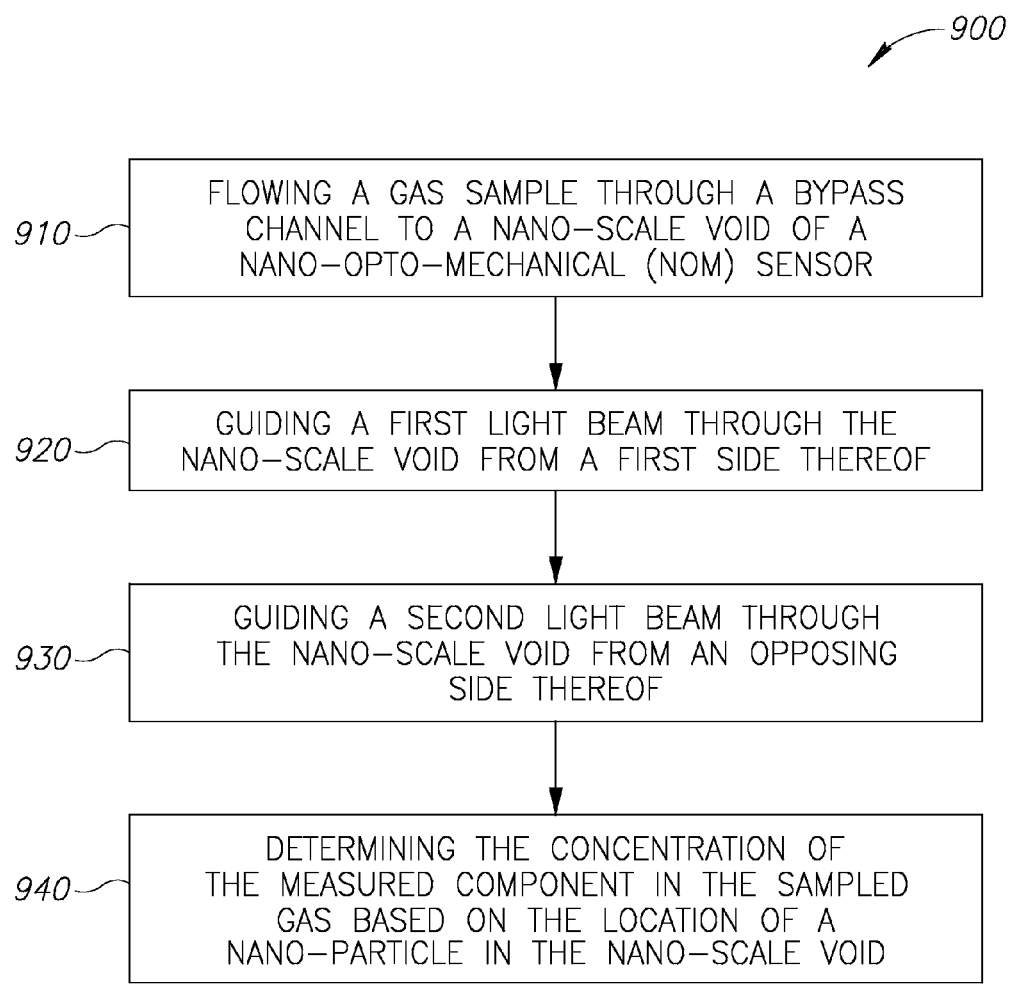
FIG. 9 schematically illustrates a flow chart of a method for measuring concentration of a component in a gas flow, according to some embodiments.

Reference is now made to FIG. 9, which schematically illustrates a flow chart of method 900 for measuring concentration of a component in a gas flow, according to some embodiments. Method 900 may include in stage 910: flowing a gas sample through a bypass channel to a nano-scale void of a nano-opto-mechanical (nom) sensor.

Method 900 may include in stage 920: guiding a first light beam through the nano-scale void from a first side thereof and in stage 930: guiding a second light beam through the nano-scale void from an opposing side thereof.

Method 900 may include in stage 940: determining the concentration of the measured component in the sampled gas based on the location of the nano-particle in the nano-scale void.

Method 900 may be used to measure intubated or non-intubated patients' exhaled/expired $CO_2$ concentration.

Figure 10:
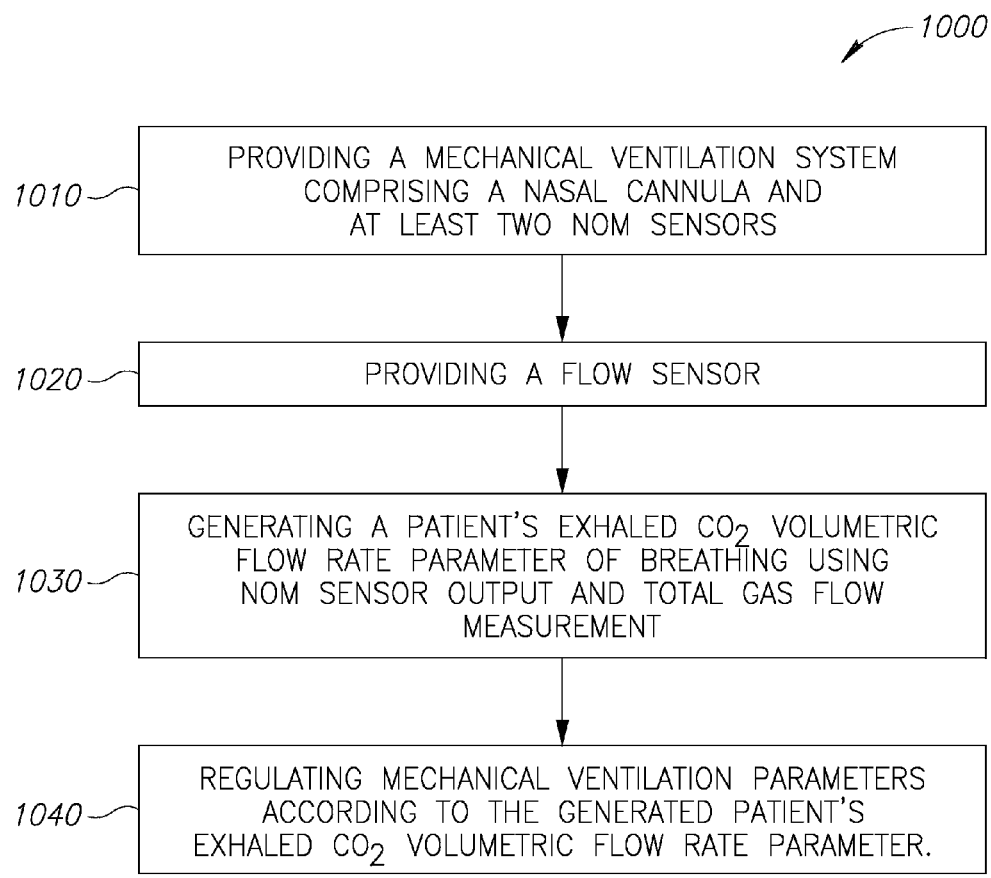
FIG. 10 schematically illustrates a flow chart of a mechanical ventilation method, according to some embodiments.

Reference is now made to FIG. 10, which schematically illustrates a flow chart of a mechanical ventilation method 1000, according to some embodiments. Method 1000 may include in stage 1010: providing a mechanical ventilation system comprising a nasal cannula and at least one NOM sensor.

Method 1000 may include in stage 1020: providing a flow sensor and in stage 1030: generating a patient's exhaled $CO_2$ volumetric flow rate parameter of breathing using the NOM sensor output and the total gas flow measurement.

Method 1000 may include in stage 1040: regulating mechanical ventilation parameters according to the generated patient's exhaled $CO_2$ volumetric flow rate parameter. The regulating may include regulating oxygen flow rate, oxygen volume or pressure, oxygen injection synchrony with exhaled air timings and other mechanical ventilation system parameters.

While a number of exemplary aspects and embodiments have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What we claim is:

1. A Nano-Opto-Mechanical (NOM) sensor for measuring concentration of a component in a gas flow, the sensor comprising:
   a bypass channel fluidly connected to a gas sampling member, said gas sampling member configured to sample gas flow;
   a nano-scale void;
   at least one nano-particle confined in said nano-scale void;
   a first optical element and a first multimode interference (MMI) region configured to guide a first light beam through said nano-scale void from a first side thereof; and
   a second optical element and a second MMI region configured to guide a second light beam through said bypass channel and through said nano-scale void from an opposing side thereof,
   wherein said first and second light beams are configured to generate interference fringes affecting the location of said nano-particle in said nano-scale void, wherein said location of said nano-particle is indicative of the concentration of the measured component in the sampled gas.

2. The NOM sensor of claim 1, further comprising a detection member configured to detect the location of said nano-particle.

3. The NOM sensor of claim 2, wherein said detection member is configured to detect a change in the location of said nano-particle.

4. The NOM sensor of claim 2, wherein said detection member comprises a third optical element configured to guide a third light beam through said nano-scale void wherein the output intensity of said third light beam is indicative of said concentration of said gas component.

5. The NOM sensor of claim 4, wherein detecting the location of said nano-particle comprises detecting the output intensity of said third light beam.

6. The NOM sensor of claim 4, wherein said third light beam is configured to pass through said nano-scale void in substantially perpendicular direction relative to the direction of said first and second light beams.

7. The NOM sensor of claim 1, wherein said nano-particle comprises gold.

8. The NOM sensor of claim 1, wherein said gas is exhaled breath and said gas component is exhaled $CO_2$; and wherein the location of said nanoparticle is indicative of said exhaled $CO_2$ concentration.

9. The NOM sensor of claim 1, wherein said first and second light beams are generated by a single light source split to two light beams.

10. The NOM sensor of claim 4, wherein said first, second and third light beams are generated by one or more light sources embedded in said NOM sensor.

11. The NOM sensor of claim 4, further comprises a flow sensor configured to measure the total gas flow, and wherein said third light output intensity and said flow sensor simultaneous measurements are used to generate a temporal $CO_2$ volumetric flow rate parameter of breathing.

12. The NOM sensor of claim 1, wherein at least two nano-particles are confined in said nano-scale void.

13. A breath sampling system, said system comprising:
   an oral/nasal cannula configured to sample breath flow from a subject; and
   one or more Nano-Opto-Mechanical (NOM) sensors for measuring concentration of a component in a gas flow, the sensor comprising:
   a bypass channel fluidly connected to said oral/nasal cannula;
   a nano-scale void;
   at least one nano-particle confined in said nano-scale void;

a first optical element and a first multimode interference (MMI) region configured to guide a first light beam through said nano-scale void from a first side thereof; and a second optical element and a second MMI region configured to guide a second light beam through said bypass channel and through said nano-scale void from an opposing side thereof, wherein said first and second light beams are configured to generate interference fringes affecting the location of said nano-particle in said nano-scale void, wherein said location of said nano-particle is indicative of the concentration of the measured component in the sampled gas.

14. The system of claim 13, wherein said oral/nasal cannula comprises an oral mouthpiece, and one or two nasal prongs and wherein said system comprises a NOM sensor for each one of said oral mouthpiece and one or two nasal prongs for measuring oral and nasal exhaled $CO_2$ concentration, respectively.

15. The system of claim 13, further comprising a detection member configured to detect the location of said nano-particle in said nano-scale void, said detection member comprising a third optical element configured to guide a third light beam through said nano-scale void wherein the output intensity of said third light beam is a function of exhaled $CO_2$.

16. The system of claim 15, wherein said detection member is configured to detect a change in the location of said nano-particle.

17. The system of claim 15, wherein detecting said location of said nano-particle comprises detecting the output intensity of said third light beam.

18. A method for measuring concentration of a component in a gas flow, the method comprising:

flowing a gas sample through a bypass channel to a nano-scale void of a Nano-Opto-Mechanical (NOM) sensor, the nano-scale void comprising a nano particle;

guiding a first light beam through the nano-scale void from a first side thereof;

guiding a second light beam through the nano-scale void from an opposing side thereof;

determining the concentration of the measured component in the sampled gas based on the location of the nano-particle in the nano-scale void.

19. The method of claim 18, wherein said component in said gas flow is exhaled $CO_2$.

20. The method of claim 18, wherein determining the concentration of the measured component in the sampled gas is based on a change in the location of said nano-particle in said nano-scale void.

* * * * *